US010827944B2

(12) United States Patent
Justice et al.

(10) Patent No.: US 10,827,944 B2
(45) Date of Patent: Nov. 10, 2020

(54) RING-SHAPED SKIN SENSOR

(71) Applicant: Microsoft Technology Licensing, LLC, Redmond, WA (US)

(72) Inventors: Gregory Kim Justice, Redmond, WA (US); Farah Shariff, Kirkland, WA (US); Scott Dallmeyer, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 321 days.

(21) Appl. No.: 15/800,756

(22) Filed: Nov. 1, 2017

(65) Prior Publication Data

US 2018/0116547 A1    May 3, 2018

Related U.S. Application Data

(63) Continuation of application No. 14/292,484, filed on May 30, 2014, now Pat. No. 9,833,164.

(51) Int. Cl.
*A61B 5/00* (2006.01)
*A61B 5/0205* (2006.01)
(Continued)

(52) U.S. Cl.
CPC .......... *A61B 5/0533* (2013.01); *A61B 5/0205* (2013.01); *A61B 5/02427* (2013.01);
(Continued)

(58) Field of Classification Search
CPC . A61B 5/0533; A61B 5/0205; A61B 5/02427; A61B 5/681; A61B 5/6824; A61B 5/0015; A61B 5/02416; A61B 5/02438; A61B 5/1112; A61B 5/6813; A61B 2560/0242; A61B 2560/0468; A61B 2562/0223; A61B 2562/06; A61B 2562/14
(Continued)

(56) References Cited

U.S. PATENT DOCUMENTS 4,182,346 A * 1/1980 Allison ................ A61B 5/0408
600/392
6,031,603 A * 2/2000 Fine .................... A61B 5/14552
356/41
(Continued)

FOREIGN PATENT DOCUMENTS

DE    102011112226 A1    5/2013
WO      03017834 A1      8/2003
(Continued)

OTHER PUBLICATIONS

"Samsung Gear Fit, Gear 2 and Gear 2 Neo go on sale worldwide", NDTV Gadgets, Retrieved from http://gadgets.ndtv.com/olhers/news/samsung-gear-fit-gear-2-and-gear-2-neo-go-on-sale-worldwide-507220, Apr. 11, 2014, 3 Pages.
(Continued)

*Primary Examiner* — Erin M Piateski
(74) *Attorney, Agent, or Firm* — Alleman Hall Creasman & Tuttle LLP

(57) ABSTRACT

A sensory-and-logic system includes a ring-shaped, electrically-conductive skin sensor sized and shaped to form an electrical connection with human skin, and an electrical component surrounded by the ring-shaped, electrically-conductive skin sensor.

18 Claims, 3 Drawing Sheets

(51) Int. Cl.
*A61B 5/024* (2006.01)
*A61B 5/053* (2006.01)
*A61B 5/11* (2006.01)

(52) U.S. Cl.
CPC ............ *A61B 5/681* (2013.01); *A61B 5/6824* (2013.01); *A61B 5/0015* (2013.01); *A61B 5/02416* (2013.01); *A61B 5/02438* (2013.01); *A61B 5/1112* (2013.01); *A61B 5/6813* (2013.01); *A61B 2560/0242* (2013.01); *A61B 2560/0468* (2013.01); *A61B 2562/0223* (2013.01); *A61B 2562/06* (2013.01); *A61B 2562/14* (2013.01)

(58) Field of Classification Search
USPC .......................................................... 600/31
See application file for complete search history.

(56) References Cited

U.S. PATENT DOCUMENTS

| | | | |
|---|---|---|---|
| 8,140,143 B2 | 3/2012 | Picard et al. | |
| 8,332,020 B2 | 12/2012 | Zdeblick | |
| 2003/0144723 A1* | 7/2003 | Andino | A61N 1/0468 607/142 |
| 2003/0233130 A1* | 12/2003 | Padmanabhan | A61N 1/3622 607/9 |
| 2004/0044390 A1* | 3/2004 | Szeles | A61H 39/002 607/142 |
| 2004/0181141 A1* | 9/2004 | Kislov | A61B 5/02116 600/393 |
| 2006/0009698 A1 | 1/2006 | Banet et al. | |
| 2007/0112404 A1* | 5/2007 | Mann | A61N 1/0551 607/116 |
| 2007/0179376 A1* | 8/2007 | Gerder | A61B 5/0006 600/393 |
| 2008/0167573 A1 | 7/2008 | Stivoric et al. | |
| 2008/0294058 A1* | 11/2008 | Shklarski | A61B 5/02055 600/502 |
| 2009/0240106 A1* | 9/2009 | Solanki | A61N 1/0551 600/104 |
| 2011/0098583 A1 | 4/2011 | Pandia et al. | |
| 2012/0283732 A1* | 11/2012 | Lam | A61B 17/00491 606/49 |
| 2012/0302856 A1* | 11/2012 | Chang | A61B 5/0028 600/378 |
| 2012/0316455 A1 | 12/2012 | Rahman et al. | |
| 2012/0330395 A1* | 12/2012 | Dar | A61B 5/1038 607/149 |
| 2013/0338470 A1 | 12/2013 | Ouwerkerk | |
| 2014/0142403 A1 | 5/2014 | Brumback et al. | |
| 2014/0143064 A1* | 5/2014 | Tran | A61B 5/0022 705/14.66 |
| 2014/0171158 A1* | 6/2014 | Setlak | G01N 27/02 455/575.1 |
| 2014/0206976 A1* | 7/2014 | Thompson | A61B 5/0006 600/391 |
| 2014/0378853 A1* | 12/2014 | McKinney | A61B 5/02438 600/509 |
| 2015/0031964 A1* | 1/2015 | Bly | A61B 5/7465 600/301 |
| 2015/0202452 A1* | 7/2015 | Skiera | A61F 2/0077 604/23 |
| 2016/0054219 A1* | 2/2016 | Blaha | G01N 33/0057 250/338.1 |

FOREIGN PATENT DOCUMENTS

| | | |
|---|---|---|
| WO | 2006018833 A2 | 2/2006 |
| WO | 2011083409 A1 | 7/2011 |
| WO | 2012125425 A2 | 9/2012 |
| WO | 2013080075 A1 | 6/2013 |

OTHER PUBLICATIONS

Goode, Lauren., "Samsung's New Gear Fit Needs to Work on the "Fit" Part", Retrieved from http://recode.nel/2014/04/08/samsungs-new-gear-fit-needs-to-work-on-the-fit-part/, Apr. 8, 2014, 10 Pages.

"Non Final Office Action Issued in U.S. Appl. No. 14/292,484", dated Oct. 25, 2016, 10 Pages.

"First Office Action and Search Report Issued in Chinese Patent Application No. 201580028881.0", dated Feb. 27, 2019, 17 Pages.

Fingas, Jon, "Tom Tom's new GPS watches track your heart rate without a chest strap (update: US pricing)", Retrieved from http://www.engadgel.com/2014/04/03/lomtom-cardio-gps-watches/, Apr. 3, 2014, 10 Pages.

"International Search Report and Written Opinion Issued in PCT Application No. PCT/US2015/032501", dated Jul. 28, 2015, 11 Pages.

Poeter, Damon, "Meet Simband, Samsung's Next-Gen Health Tracker", Retrieved from http://www.pcmag.com/article2/0,2817,2458663,00.asp, May 28, 2014, 5 Pages.

Wall, Matt., "Seriously cool toys—Tobii mobile eye-tracking glasses, Pivothead HD video-recording eye-wear, and the Affectiva Q-sensor", Retrieved from http://computingforpsychologists.wordpress.com/tag/galvanic-skin-response/, Jul. 11, 2012, 4 Pages.

"Office Action Issued in European Patent Application No. 15728697.2", dated Feb. 21, 2020, 6 Pages.

* cited by examiner

RING-SHAPED SKIN SENSOR

CROSS-REFERENCE TO RELATED APPLICATIONS

This application is a continuation of U.S. patent application Ser. No. 14/292,484, filed May 30, 2014, now U.S. Pat. No. 9,833,164, issued Dec. 5, 2017, the entire contents of which is hereby incorporated herein by reference for all purposes.

BACKGROUND

Electrically-conductive skin sensors may be incorporated into a wide variety of electronic devices.

DETAILED DESCRIPTION

Figure 1A:
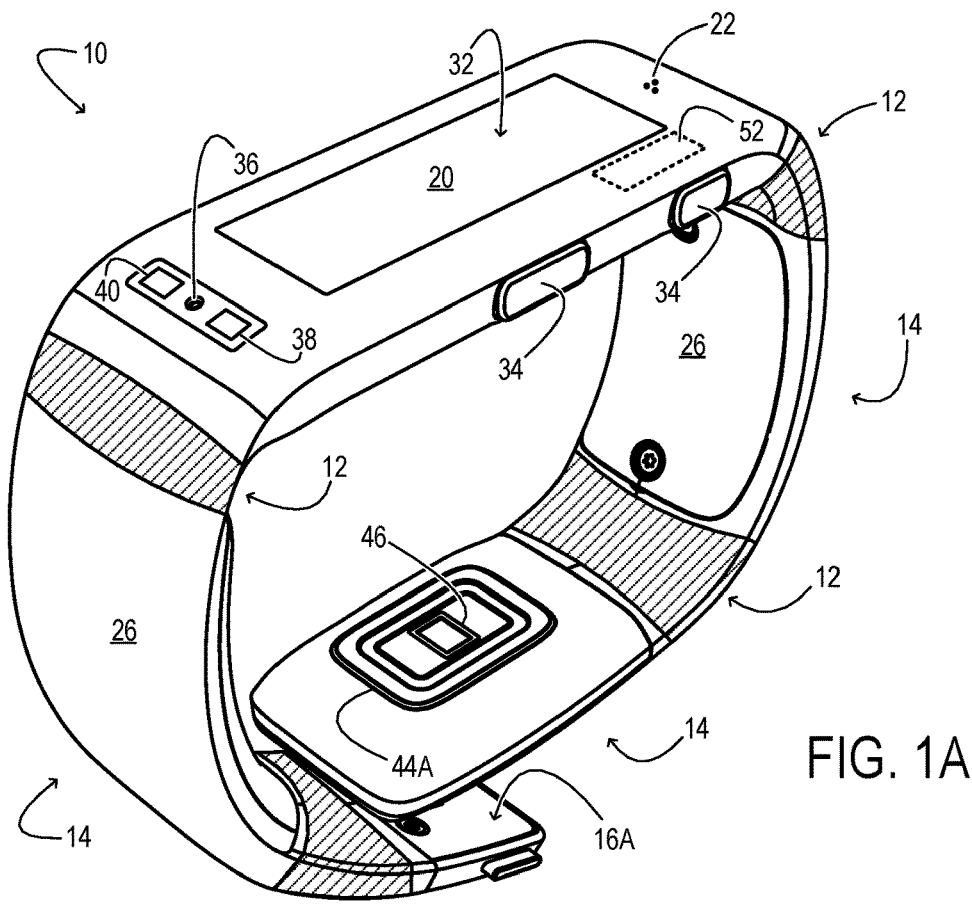
FIGS. 1A, 1B, 2A, and 2B show an exemplary wearable electronic device.

Electrically-conductive skin sensors, also referred to as Galvanic Skin Response (GSR) contacts, may be included in a wearable electronic device, such as a wrist band. The GSR contacts may be used, for example, to detect the stress level or other characteristic of the wearer of the device. Two electrically-conductive skin sensors included to measure the resistance of the skin may provide a more accurate measurement if held in constant contact with the skin of the wearer. However, given the movement of the wrist as well as differing shapes and sizes of wrists of different users, it may be difficult to maintain both sensors in close contact with the skin. To provide an accurate measurement of the resistance of a user's skin, some electrically-conductive skin sensors may be made large and knobby to improve contact with the skin of the user.

In another example, a sensory-and-logic system comprises a ring-shaped, electrically-conductive skin sensor sized and shaped to form an electrical connection with human skin, and an electrical component surrounded by the ring-shaped, electrically-conductive skin sensor.

The electrically-conductive skin sensors may be ring-shaped in order to substantially surround a desired electrical component. In some examples, the desired electrical component is a component that also must be positioned proximate the skin of the wearer, such as an optical heart rate sensor. Thus, by providing the electrically-conductive skin sensor around another body-sensing component, the electrically-conductive skin sensor may be held in contact with the skin along with the additional body-sensing component. Additionally, in some examples, the desired electrical component may be inflexible, such as an optical heart rate sensor, power connector, or other component. By architecturally aligning the inflexible electrically-conductive skin sensors with other components of the wearable electronic device that are inflexible, the number of inflexible regions present in the wearable electronic device may be reduced. This may benefit the user experience by providing a more flexible and comfortable wearable device.

One electrically-conductive skin sensor may be positioned on a first side of the wearable electronic device (e.g., underside of the wrist) while the other electrically-conductive skin sensor may be positioned on the opposing side of the device (e.g., topside of the wrist). The flexibility and latching aspects of the wearable electronic device may be configured such that the two electrically-conductive skin sensors are held in close contact with the skin of the wearer.

While described below in the context of a portable wearable electronic device, the examples of the electrically-conductive skin sensor of this disclosure may be implemented with different types of sensor and logic systems. For example, the electrically-conductive skin sensor may be used in stationary or mobile equipment not intended to be worn by the user, and instead, intended to be contacted by the user by placing a body part, e.g., a hand or foot, on the electrically-conductive skin sensor.

Figure 1B:
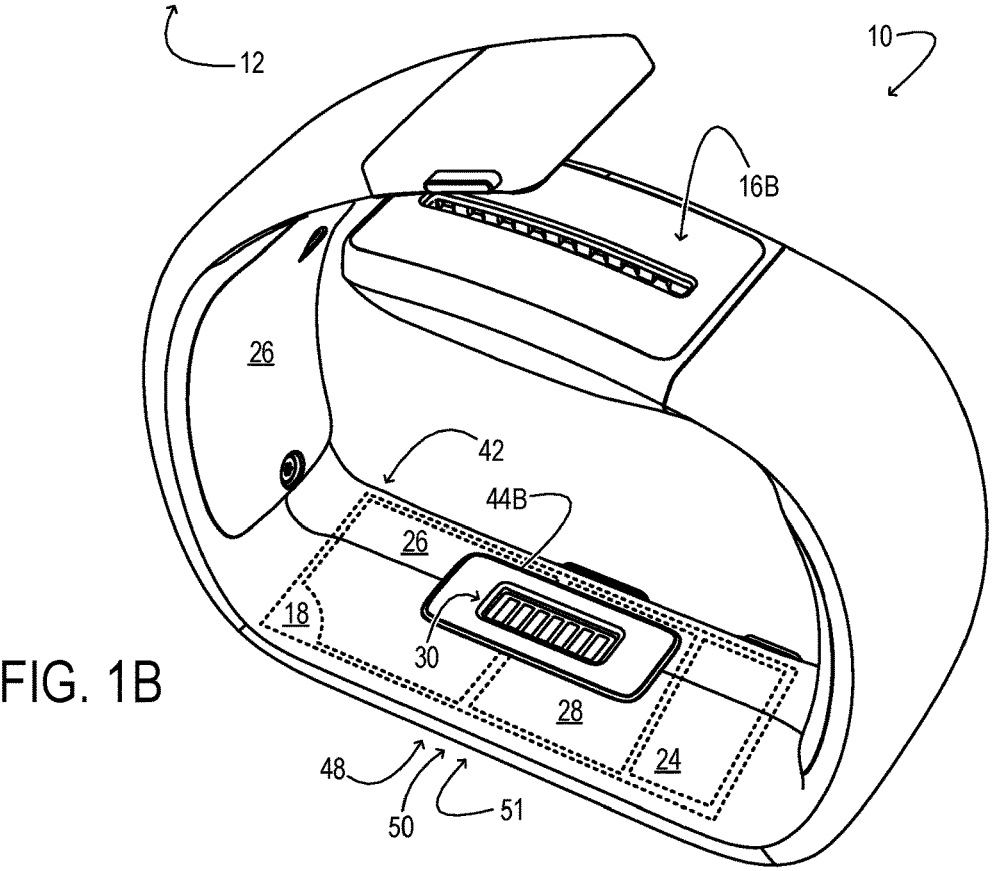

FIGS. 1A and 1B show aspects of an example sensory-and-logic system in the form of a wearable electronic device 10. The illustrated device is band-shaped and may be worn around a wrist. Device 10 includes at least four flexion regions 12 linking less flexible regions 14. The flexion regions of device 10 may be elastomeric in some examples. Fastening componentry 16A and 16B is arranged at both ends of the device. The flexion regions and fastening componentry enable the device to be closed into a loop and to be worn on a user's wrist. In other implementations, wearable electronic devices of a more elongate band shape may be worn around the user's bicep, waist, chest, ankle, leg, head, or other body part. The device, for example, may take the form of eye glasses, a head band, an arm-band, an ankle band, a chest strap, or an implantable device to be implanted in tissue.

Wearable electronic device 10 includes various functional components integrated into regions 14. In particular, the electronic device includes a compute system 18, display 20, loudspeaker 22, communication suite 24, and various sensors. These components draw power from one or more energy-storage cells 26. A battery—e.g., a lithium ion battery—is one type of energy-storage cell suitable for this purpose. Examples of alternative energy-storage cells include super- and ultra-capacitors. In devices worn on the user's wrist, the energy-storage cells may be curved to fit the wrist, as shown in the drawings.

In general, energy-storage cells 26 may be replaceable and/or rechargeable. In some examples, recharge power may be provided through a universal serial bus (USB) port 30, which includes a magnetic latch to releasably secure a complementary USB connector. In other examples, the energy storage cells may be recharged by wireless inductive or ambient-light charging. In still other examples, the wearable electronic device may include electro-mechanical componentry to recharge the energy storage cells from the user's adventitious or purposeful body motion. For example, batteries or capacitors may be charged via an electromechanical generator integrated into device 10. The generator may be turned by a mechanical armature that turns while the user is moving and wearing device 10.

In wearable electronic device 10, compute system 18 is situated below display 20 and operatively coupled to the display, along with loudspeaker 22, communication suite 24, and the various sensors. The compute system includes a data-storage machine 27 to hold data and instructions, and a logic machine 28 to execute the instructions. Aspects of the compute system are described in further detail with reference to FIG. 3.

Display 20 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be frontlit via ambient light. A curved display may also be used. Further, AMOLED displays or quantum dot displays may be used.

Communication suite 24 may include any appropriate wired or wireless communications componentry. In FIGS. 1A and 1B, the communications suite includes USB port 30, which may be used for exchanging data between wearable electronic device 10 and other computer systems, as well as providing recharge power. The communication suite may further include two-way Bluetooth, Wi-Fi, cellular, near-field communication and/or other radios. In some implementations, the communication suite may include an additional transceiver for optical, line-of-sight (e.g., infrared) communication.

In wearable electronic device 10, touch-screen sensor 32 is coupled to display 20 and configured to receive touch input from the user. The touch sensor may be resistive, capacitive, or optically based. Pushbutton sensors may be used to detect the state of push buttons 34, which may include rockers. Input from the pushbutton sensors may be used to enact a home-key or on-off feature, control audio volume, turn the microphone on or off, or other function.

FIGS. 1A and 1B show various other sensors of wearable electronic device 10. Such sensors include microphone 36, visible-light sensor 38, ultraviolet sensor 40, and ambient temperature sensor 42. The microphone provides input to compute system 18 that may be used to measure the ambient sound level or receive voice commands from the wearer. Input from the visible-light sensor, ultraviolet sensor, and ambient temperature sensor may be used to assess aspects of the wearer's environment—i.e., the temperature, overall lighting level, and whether the wearer is indoors or outdoors.

FIGS. 1A and 1B show a pair of ring-shaped contact sensor modules 44A and 44B, which contact the wearer's skin when wearable electronic device 10 is worn. The ring-shaped contact sensor modules may include independent or cooperating sensor elements, to provide a plurality of sensory functions. For example, the ring-shaped contact sensor modules may provide an electrical resistance and/or capacitance sensory function, which measures the electrical resistance and/or capacitance of the wearer's skin. Compute system 18 may use such input to assess whether or not the device is being worn, a stress level of the user, or other attributes. In some implementations, the sensory function may be used to determine how tightly the wearable electronic device is being worn. In the illustrated configuration, the separation between the two ring-shaped contact-sensor modules provides a relatively long electrical path length, for more accurate measurement of skin resistance. In some examples, a ring-shaped contact sensor module may also provide measurement of the wearer's skin temperature. Arranged inside ring-shaped contact sensor module 44B in the illustrated configuration is an electrical component in the form of an optical pulse rate sensor 46. The optical pulse-rate sensor may include an LED emitter and matched photodiode to detect blood flow through the capillaries in the skin and thereby provide a measurement of the wearer's pulse rate. Arranged inside ring-shaped contact sensor module 44A is an electrical component in the form of USB port 30.

Wearable electronic device 10 may also include motion sensing componentry, such as an accelerometer 48, gyroscope 50, and magnetometer 51. The accelerometer and gyroscope may furnish inertial and/or rotation rate data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation. The wearable electronic device may also include a global positioning system (GPS) receiver 52 for determining the wearer's geographic location and/or velocity. In some configurations, the antenna of the GPS receiver may be relatively flexible and extend into flexion regions 12.

Compute system 18, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

Figure 2A:
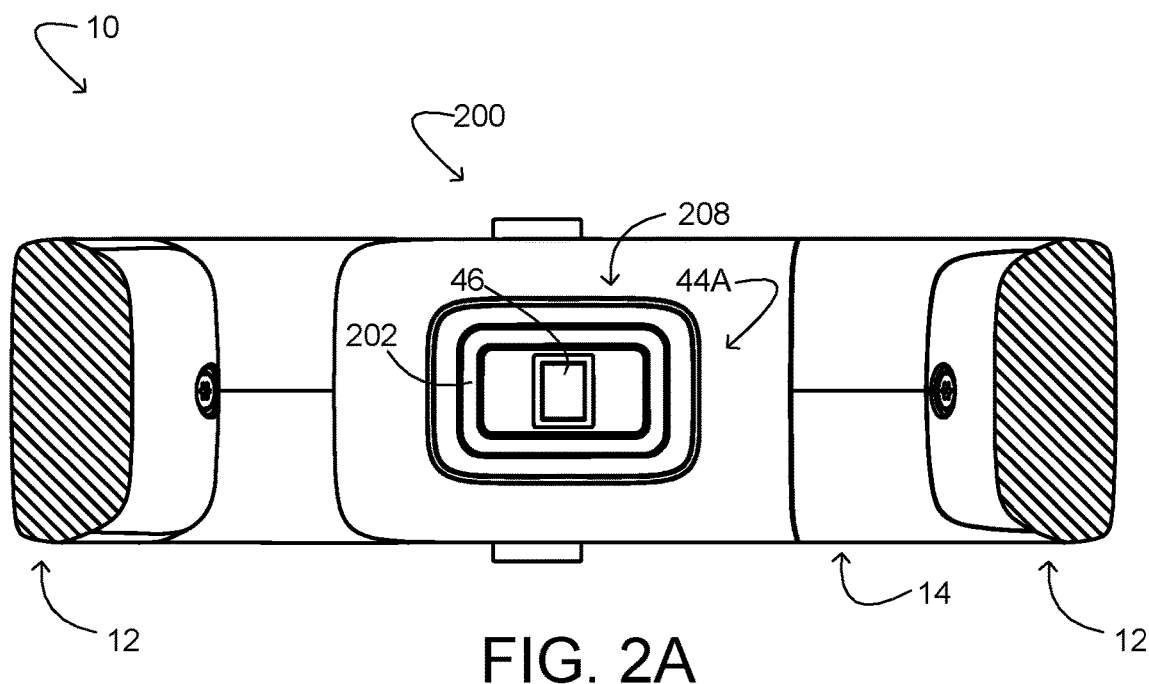
Figure 2B:
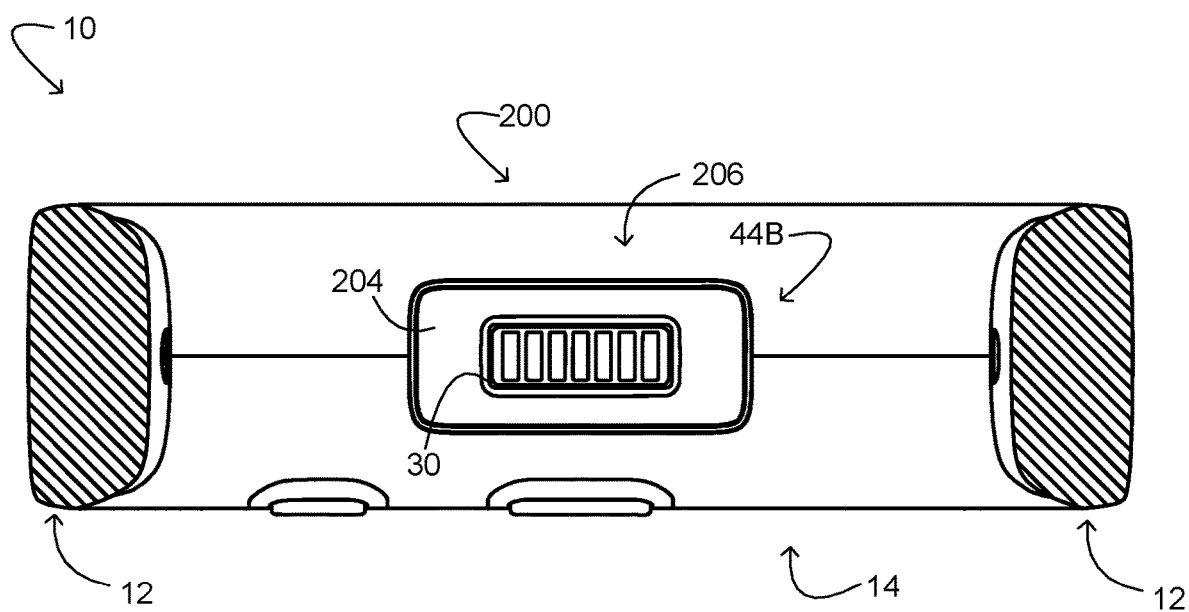

FIGS. 2A and 2B show a bottom and a top, respectively, of an inside surface of the sensory-and-logic system of FIGS. 1A and 1B (e.g., wearable electronic device 10). Wearable electronic device 10 is illustrated in the form of a wrist band, with the inside surface corresponding to the inner portion of the wrist band that faces the skin of a user when the wearable electronic device is worn by the user.

As explained above, the sensory-and-logic system may include one or more ring-shaped contact sensor modules. In one example, each contact sensor module may include an electrically-conductive skin sensor surrounding an electrical component. As illustrated in FIGS. 2A and 2B, the sensory-and-logic system includes two contact sensor modules, first contact sensor module 44A and second contact sensor module 44B, explained in detail below. Each contact sensor module is supported by a wrist band assembly 200. The wrist band assembly 200 may include one or more flexion regions 12 and one or more less flexible regions 14, as explained above.

Referring now to first contact sensor module 44A, it is included in a bottom portion of the inside surface of the wearable electronic device 10, shown in FIG. 2A. First contact sensor module 44A includes a first ring-shaped, electrically-conductive skin sensor 202, sized and shaped to contact human skin, surrounding optical pulse rate sensor 46.

First skin sensor 202 measures the electrical conductance of the skin, which varies depending on the moisture (e.g., sweat) of the skin, also referred to as the galvanic skin response or galvanic skin potential. First skin sensor 202 comprises an electrode that is electrically coupled to a device (e.g., compute system 18) configured to measure the electrical resistance between the electrode of the skin sensor and a second, distally placed electrode (included as part of second skin sensor 204, described below). The electrode may comprise an outer surface of the first skin sensor 202 and may be constructed from any suitable metal or metal alloy, such as aluminum in one example. The outward surface of the first skin sensor 202 may be finished (e.g., with a satin finish) in order to provide a smooth surface that is comfortable to the skin of a wearer. Further, in some examples, the outward surface of first skin sensor 202 may include a plurality of protrusions and/or a rough finish in order to promote contact with a wearer's skin.

First skin sensor 202 may be generally ring-shaped in order to surround the optical pulse rate sensor 46. The first skin sensor 202 may include any number of straight and/or curved segments. For example, the first skin sensor 202 may be generally rectangular with rounded corners, generally oval, generally polygonal, etc. Further, the ring-shaped skin sensor need not completely encircle an interior electrical component. For example, a U-shaped, L-shaped, or C-shaped sensor may be used.

Second contact sensor module 44B is included in a top portion of the inside of the wearable electronic device, shown in FIG. 2B. Second contact sensor module 44B includes a second ring-shaped electrically conductive skin sensor 204, sized and shaped to contact human skin, surrounding a power and data connector, such as a universal serial bus (USB) port 30.

Second skin sensor 204 may be similar to first skin sensor 202. For example, second skin sensor 204 may be generally ring-shaped in order to surround the USB port 30. The second skin sensor 204 may include any number of straight and/or curved segments, may be generally rectangular with rounded corners, generally oval, generally polygonal, U-shaped, L-shaped, C-shaped, or other shape that may provide contact with a user's skin without pinching the user or otherwise creating user discomfort.

Second skin sensor 204 also comprises an electrode that is electrically coupled to a device configured to measure the electrical resistance between the electrode of the skin sensor and a second, distally placed electrode (e.g., the electrode of first skin sensor 202). The electrode may comprise an outer surface of the second skin sensor 204 and may be constructed from any suitable metal or metal alloy, such as aluminum in one example. The outward surface of the second skin sensor 204 may be finished (e.g., with a satin finish) in order to provide a smooth surface that is comfortable to the skin of a wearer. Further, in some examples, the outward surface of second skin sensor 204 may include a plurality of protrusions and/or a rough finish in order to ensure contact with a wearer's skin and/or to facilitate a connection with a power and data connector. The first and second skin sensors may be identical to one another, or the first and second skin sensors can be different from one another (e.g., as shown in FIGS. 2A and 2B). Differences may include size, shape, material, finish, or other attributes.

USB port 30 comprises a plurality of charging contact pads for connecting to associated electrical contacts of a power and data connector. The charging contact pads may be formed of an electrically conductive material, such as gold, and disposed on a frame formed from non-electrically conductive material, such as plastic. The non-electrically conductive material may be utilized to isolate the electrical power and/or signaling provided to and from each of the charging contact pads. The charging contact pads may be electrically connected to one or more compute systems within the wearable electronic device 10. For example, a contact pad configured to receive a power signal may be electrically connected to a battery (e.g., energy storage-cell 26 of FIGS. 1A and 1B, interposed between the first and second contact sensor modules) and/or recharging system. A contact pad configured to receive a data signal may be electrically connected to a logic system and/or data-storage system of the wearable electronic device 10.

The first contact sensor module 44A and the second contact sensor module 44B may be spaced apart (e.g., located distally) from each other by a suitable distance in order to provide measurable resistance between the electrodes of the skin sensors of the contact sensor modules. Additionally, the contact sensor modules may be positioned to hold the skin sensors in close contact with the skin of the user. For example, the contact sensor modules may be integrated into opposing surfaces of the wearable electronic device such that the skin sensors are naturally held in contact with the skin on opposite sides of the wrist.

Additionally, as explained previously, the first and/or second electrically-conductive skin sensors may be incorporated into already-inflexible regions of the wearable electronic device 10, to decrease the number of inflexible regions present in the wearable electronic device. For example, as illustrated, the USB port 30 and the second electrically-conductive skin sensor 204 are constituent components of a rigid display module 206 including display 20 and additional components. Further, the optical pulse rate sensor 46 and the first electrically-conductive skin sensor 202 are constituent components of a rigid clasp module 210 including a latching mechanism to securely close the wearable electronic device 10.

In some examples, the rigid clasp module 210 includes a rigid or semi-rigid pillow to house the optical pulse rate sensor 46 and the first electrically-conductive skin sensor 202. The pillow may include a spring, flexible coating, and/or other components that elevate the optical pulse rate sensor 46 and the first electrically-conductive skin sensor 202 above the wrist band assembly 200 and urge the optical pulse rate sensor 46 and the first electrically-conductive skin sensor 202 into the skin of the wearer, ensuring a close contact between the sensors and the skin of the wearer.

Further, compute system 18 may be operably coupled to each of the first electrically-conductive skin sensor and second electrically-conductive skin sensor in order to receive output from the first and second electrically-conductive skin sensors to measure the resistance of the wearer's skin. Compute system 18 may also be operably coupled to the optical pulse rate sensor and universal serial bus port.

While first electrically-conductive skin sensor 202 is described above as surrounding an optical pulse rate monitor and positioned proximate a display (as part of the rigid display module), other configurations are possible. For example, the first electrically-conductive skin sensor 202 may surround a different electrical component of the wearable electronic device, such as the GPS receiver, accelerometer, etc., and/or be a constituent component of a different rigid module, such as a rigid battery box module. Similarly, the second electrically-conductive skin sensor 204 may surround an electrical component other than the USB port and/or be included in a different rigid module.

The electrically-conductive skin sensor and electrical component of the first contact sensor module and/or second contact sensor module may be generally co-planar in one example. In another example, the electrical component may be slightly elevated or recessed relative to the electrically-conductive skin sensor (e.g., less than 1 mm). In a still further example, the electrical component may be significantly elevated or recessed relative to the electrically-conductive skin sensor (e.g., greater than 1 mm).

As evident from the foregoing description, the methods and processes described herein may be tied to a sensory-and-logic system of one or more machines. Such methods and processes may be implemented as a computer-application program or service, an application-programming interface (API), a library, firmware, and/or other computer-program product. FIGS. 1A and 1B show one, non-limiting example of a sensory-and-logic system to enact the methods and processes described herein. However, these methods and process may also be enacted on sensory-and-logic systems of other configurations and form factors, as shown schematically in FIG. 3.

Figure 3:
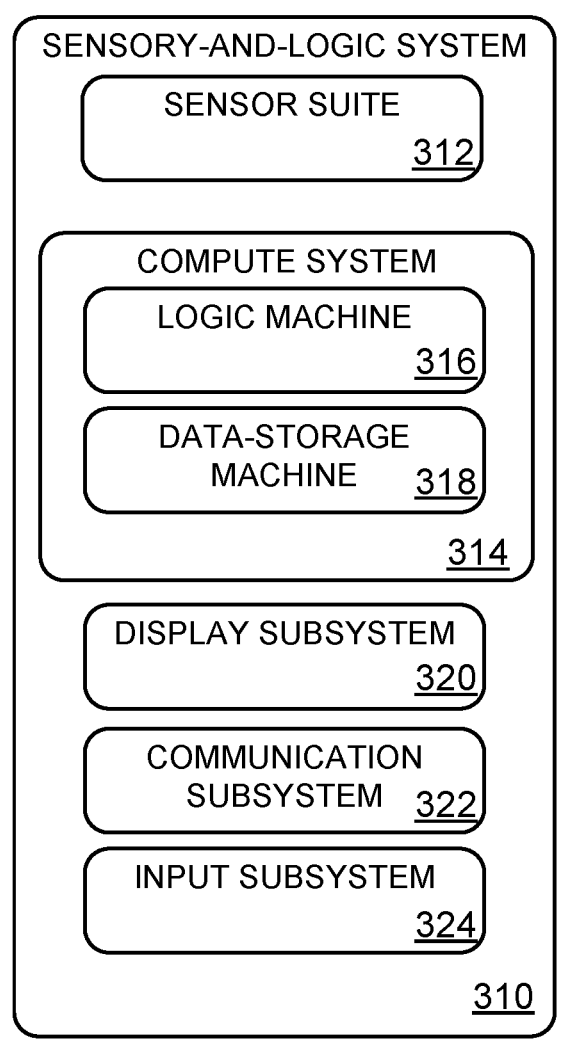
FIG. 3 is a block diagram of an example computing device.

FIG. 3 schematically shows a form-agnostic sensory-and-logic system 310 that includes a sensor suite 312 operatively coupled to a compute system 314. The compute system includes a logic machine 316 and a data-storage machine 318. The compute system is operatively coupled to a display subsystem 320, a communication subsystem 322, an input subsystem 324, and/or other components not shown in FIG. 3.

Logic machine 316 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 316 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 318 includes one or more physical devices configured to hold instructions executable by logic machine 316 to implement the methods and processes described herein. When such methods and processes are implemented, the state of the data-storage machine may be transformed—e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

It will be appreciated that data-storage machine 318 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 316 and data-storage machine 318 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 320 may be used to present a visual representation of data held by data-storage machine 318. This visual representation may take the form of a graphical user interface (GUI). As the herein described methods and processes change the data held by the storage machine, and thus transform the state of the storage machine, the state of display subsystem 320 may likewise be transformed to visually represent changes in the underlying data. Display subsystem 320 may include one or more display subsystem devices utilizing virtually any type of technology. Such display subsystem devices may be combined with logic machine 316 and/or data-storage machine 318 in a shared enclosure, or such display subsystem devices may be peripheral display subsystem devices. Display 20 of FIGS. 1A and 1B is an example of display subsystem 320.

Communication subsystem 322 may be configured to communicatively couple compute system 314 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 24 of FIGS. 1A and 1B is an example of communication subsystem 322.

Input subsystem 324 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Touch screen sensor 32 and push buttons 34 of FIGS. 1A and 1B are examples of input subsystem 324.

Sensor suite 312 may include one or more different sensors—e.g., a touch-screen sensor, push-button sensor, microphone, visible-light sensor, ultraviolet sensor, ambient-temperature sensor, contact sensors, optical pulse-rate sensor, accelerometer, gyroscope, magnetometer, and/or GPS receiver—as described above with reference to FIGS. 1A and 1B.

It will be understood that the configurations and approaches described herein are exemplary in nature, and that these specific implementations or examples are not to be taken in a limiting sense, because numerous variations are feasible. The specific routines or methods described herein may represent one or more processing strategies. As such, various acts shown or described may be performed in the sequence shown or described, in other sequences, in parallel, or omitted.

The subject matter of this disclosure includes all novel and non-obvious combinations and sub-combinations of the various processes, systems and configurations, and other features, functions, acts, and/or properties disclosed herein, as well as any and all equivalents thereof.

The invention claimed is:

1. A sensory-and-logic system, comprising:
a power and data connector; and
a ring-shaped, electrically-conductive skin sensor surrounding the power and data connector, the ring-shaped, electrically-conductive skin sensor sized and shaped to form an electrical connection with human skin.

2. The sensory-and-logic system of claim 1, wherein the power and data connector includes a universal serial bus port.

3. The sensory-and-logic system of claim 1, further comprising a wrist band assembly supporting the power and data connector and the ring-shaped, electrically-conductive skin sensor.

4. The sensory-and-logic system of claim 1, wherein the ring-shaped, electrically-conductive skin sensor is a first ring-shaped, electrically-conductive skin sensor, and further comprising a second ring-shaped, electrically-conductive skin sensor distally located relative to the first ring-shaped, electrically-conductive skin sensor.

5. The sensory-and-logic system of claim 4, wherein the first ring-shaped, electrically-conductive skin sensor and the second ring-shaped, electrically-conductive skin sensor are distally supported by opposing portions of a wrist band assembly.

6. The sensory-and-logic system of claim 4, wherein the second ring-shaped, electrically conductive skin sensor surrounds an optical pulse rate sensor.

7. A sensory-and-logic system, comprising:
a universal serial bus port; and
a ring-shaped, electrically-conductive skin sensor surrounding the universal serial bus port, the ring-shaped, electrically-conductive skin sensor sized and shaped to form an electrical connection with human skin.

8. The sensory-and-logic system of claim 7, further comprising a wrist band assembly supporting the universal serial bus port and the ring-shaped, electrically-conductive skin sensor.

9. The sensory-and-logic system of claim 7, wherein the ring-shaped, electrically-conductive skin sensor is a first ring-shaped, electrically-conductive skin sensor, and further comprising a second ring-shaped, electrically-conductive skin sensor distally located relative to the first ring-shaped, electrically-conductive skin sensor.

10. The sensory-and-logic system of claim 9, wherein the first ring-shaped, electrically-conductive skin sensor and the second ring-shaped, electrically-conductive skin sensor are distally supported by opposing portions of a wrist band assembly.

11. The sensory-and-logic system of claim 9, wherein the second ring-shaped, electrically conductive skin sensor surrounds an optical pulse rate sensor.

12. A sensory-and-logic system, comprising:
a wrist-band assembly including opposing first and second portions;
a first ring-shaped, electrically conductive skin sensor arranged on the first portion, the first ring-shaped, electrically conductive skin sensor being sized and shaped to form an electrical connection with human skin;
a second ring-shaped, electrically conductive skin sensor arranged on the second portion, distally with respect to the first ring-shaped, electrically conductive skin sensor, the second ring-shaped, electronically conductive skin sensor being sized and shaped to form an electrical connection with human skin;
componentry configured to measure electrical resistance along a path between the first ring-shaped, electrically conductive skin sensor and the second ring-shaped, electrically conductive skin sensor;
a first electrical component surrounded by the first ring-shaped, electrically conductive skin sensor and configured to receive electrical power; and
a second electrical component surrounded by the second ring-shaped, electrically conductive skin sensor.

13. The sensory-and-logic system of claim 12, wherein the first electrical component includes a power and data connector.

14. The sensory-and-logic system of claim 13, wherein the power and data connector includes a universal serial bus port.

15. The sensory-and-logic system of claim 12, wherein the second electrical component includes an optical pulse-rate sensor.

16. The sensory-and-logic system of claim 15, further comprising a third sensor, distinct from the first and second ring-shaped, electrically conductive skin sensors and from the optical pulse-rate sensor.

17. The sensory-and-logic system of claim 16, wherein the third sensor is a light sensor.

18. The sensory-and-logic system of claim 15, further comprising a compute system operably coupled to the first and second ring-shaped, electrically conductive skin sensors and to the optical pulse-rate sensor.

* * * * *